United States Patent [19]

Cusic et al.

[11] 3,981,875

[45] Sept. 21, 1976

[54] 2-SUBSTITUTED-9-PHENYL-2,3,4,4A,9,9A-HEXAHYDRO-1H-INDENO[2,1-C]PYRIDINES AND RELATED COMPOUNDS

[75] Inventors: John W. Cusic, Skokie; Charles R. Ellefson, Chicago; Chi Min Woo, Skokie, all of Ill.

[73] Assignee: G. D. Searle & Co., Chicago, Ill.

[22] Filed: June 16, 1975

[21] Appl. No.: 587,405

[52] U.S. Cl............................ 260/293.54; 424/263; 424/267; 260/293.59; 260/296 T
[51] Int. Cl.².............. C07D 401/06; C07D 221/16
[58] Field of Search............. 260/293.54, 293.59, 260/296 T

[56] References Cited
UNITED STATES PATENTS 2,470,109  5/1949  Plati et al....................... 260/293.54
2,546,652  3/1951  Plati et al....................... 260/293.54

FOREIGN PATENTS OR APPLICATIONS 1,175,676  12/1969  United Kingdom............ 260/293.54

Primary Examiner—Norma S. Milestone
Attorney, Agent, or Firm—John J. Kolano

[57] ABSTRACT

2-Substituted-9-phenyl-2,3,4,4a,9,9a-hexahydro-1H-indeno[2,1-c]pyridines having anti-arrhythmic activity are described herein. The subject compounds can be prepared by reduction of the corresponding 2-Substituted-9-phenyl-2,3-dihydro-1H-indeno[2,1-c]pyridines. The compounds additionally display antibacterial activity.

15 Claims, No Drawings

2-SUBSTITUTED-9-PHENYL-2,3,4,4A,9,9A-HEXAHYDRO-1H-INDENO[2,1-C]PYRIDINES AND RELATED COMPOUNDS

The present invention relates to a group of 2-substituted--9-phenyl-2,3,4,4a,9,9a-hexahydro-1H-indeno[2,1-c]pyridines and their corresponding 2,3-dihydro analogs. More particularly, the present invention relates to a group of compounds having the general formula

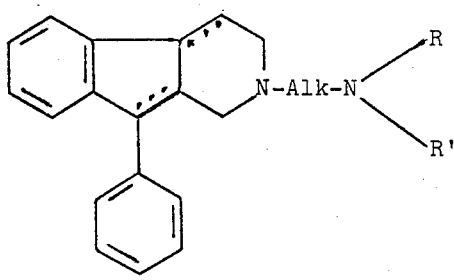

(I)

wherein Alk is alkylene of 2 to 6 carbon atoms separating the nitrogen atoms attached thereto by at least 2 carbon atoms; NRR' is selected from the group consisting of di(lower alkyl)amino, pyrrolidino, piperidino, and hexamethylenimino, and the dotted lines indicate the presence of a set of optional double bonds.

The lower alkyl groups referred to above contain 1 to 6 carbon atoms and are exemplified by methyl, ethyl, propyl, isopropyl and the like. The alkylene groups referred to above contain 2 to 6 carbon atoms and can be exemplified by groups such as ethylene, propylene, trimethylene and 1,4-pentylene.

Equivalent to the compounds of formula (I) for the purposes of this invention are the pharmaceutically acceptable acid addition and quaternary ammonium salts thereof. Such acid addition salts can be derived from a variety of organic and inorganic acids such as sulfuric, phosphoric, hydrochloric, hydrobromic, hydroiodic, sulfamic, citric, lactic, maleic, succinic, tartaric, cinnamic, acetic, benzoic, gluconic, ascorbic and related acids. Similarly, the quaternary ammonium salts can be derived from a variety of organic esters of sulfuric, hydrohalic and aromatic sulfonic acids. Among such esters are methyl chloride and bromide, ethyl chloride, propyl chloride, butyl chloride, isobutyl chloride, benzyl chloride and bromide, phenethyl bromide, naphthylmethyl chloride, dimethyl sulfate, methyl benzenesulfonate, ethyl toluenesulfonate, ethylene chlorohydrin, propylene chlorohydrin, allyl bromide, methallyl bromide and crotyl bromide. Also equivalent to the compounds of formula (I) are solvates thereof in which the solvents are present in biologically insignificant amounts.

The compounds of this invention are useful because of their pharmacological properties. In particular, they possess activity as anti-arrhythmic agents. Thus, they bring about a return to normal heart rhythm in animals in which the heart rhythm has become irregular.

The anti-arrhythmic utility of the instant compounds is evident from the results of a standardized test for their capacity to slow the ventricular tachycardia induced by aconitine in the isolated rabbit heart. The procedure is essentially that described by Lucchesi [J. Pharmacol. Exp. Therap., 137, 291 (1962], modified in certain particulars as follows: Hearts are obtained from adult albino rabbits of either sex and perfused in apparatus modeled after that devised by Anderson and Craver [J. Pharmacol. Exp. Therap., 93, 135 (1948)]. The composition of the perfusion solution is the same as Lucchesi's, but the volume is increased to 200 ml. and the temperature lowered to 28°C. Aconitine (ordinarily as the nitrate) is administered as soon as the heart beat is regular and the EKG pattern normal, the dose being so selected as to at least double the rate. Typically, 0.05 ml. of 0.1 percent aconitine nitrate in physiological saline is injected. EKG's are recorded at 5 minute intervals after onset of ventricular tachycardia until two successive readings show stabilization of the rate. Perfusate collected during this time is discarded and replaced with fresh solution q.s. 200 ml. Promptly following stabilization, 2 mg. of compound dissolved or suspended in 1 ml. of physiological saline is mixed with the perfusion solution. Ten minutes later a like amount is introduced, followed after a further ten minutes by double the first amount. Final concentration of compound in the perfusion solution is thus 40 mg. per liter. Recording of EKG's is continued at five minute intervals throughout this time and for 10 minutes thereafter. A compound is considered anti-arrhythmic if, at any time during the 30 minutes immediately following initial administration in at least half of a minimum of two tests, it reduces by 50 percent or more the rate recorded 10 minutes after onset of tachycardia. Among the compounds of this invention, the following representative compounds have been found active: 2,3-dihydro-2-piperidinopropyl-9-phenyl-1H-indeno[2,1-c]pyridine dihydrobromide hemihydrate, cis-2,3,4,4a,9,9a-hexahydro-2-(3-diethylaminopropyl)-9-cis-phenyl-1H-indeno[2,1-c]pyridine dihydrochloride hemihydrate, and cis-2,3,4,4a,9,9a-hexahydro-2-(3-dimethylaminopropyl)-9-cis-phenyl-1H-indeno[2,1-c]pyridine dihydrochloride hemihydrate.

A further test demonstrating the anti-arrhythmic utility of the present compounds is as follows:

Male mongrel dogs are connected to a physiograph to follow heart and blood action. At the onset of the testing, an initial dose of 40 mcg./kg. ouabain is administered intravenously in a saline solution. This is followed 30 minutes later by a dose of 20 mcg./kg. of ouabain and, at 15 minute intervals, by a dose of 10 mcg./kg. of ouabain until ventricular arrhythmia occurs and persists for twenty minutes. Then, a saline solution of test compound is administered at a dose of 5 mg./kg. If the heart action does not become normal, additional test compound is administered at a dose of 5 mg./kg. at 15 minute intervals until heart action becomes normal or until the total dose of test compound administered is 20 mg./kg. The procedure is run in two dogs. A compound is considered anti-arrhythmic if it causes a return to normal heart action for a period of 15 minutes or more in half or more of the dogs tested at a dose of 20 mg./kg. or less. An additional compound which shows activity in this test is cis-2,3,4,4a,9,9a-hexahydro-2-(3-piperidino-propyl)-9-trans-phenyl-1H-indeno[2,1-c]pyridine.

In view of their potent pharmacological properties, the compounds of this invention can be combined with pharmaceutical carriers and administered in a variety of well-known pharmaceutical forms suitable for oral or parenteral administration.

The compounds of the present invention also possess antibacterial activity against a variety of microorganisms. Thus, they inhibit the growth of bacteria such as *Staphylococcus aureus*, *Escherichia coli* and *Bacteroides fragilis*. By virtue of their antibacterial activity, these compounds can be combined with various known excipients and adjuvants in the form of dusts, solutions, suspensions, ointments, and sprays to provide compositions useful for disinfecting purposes.

The 2,3-dihydro compounds of the present invention are conveniently prepared by contacting a compound of the formula

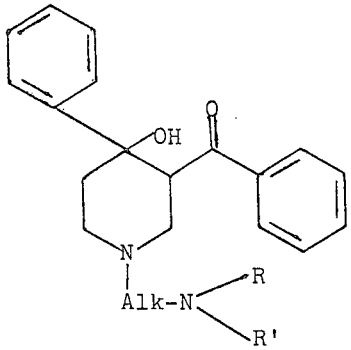

(II)

wherein Alk and NRR' are defined as hereinabove, with a strong mineral acid. Suitable strong mineral acids include, but are not limited to hydrobromic, hydrochloric and sulfuric. A particularly suitable mineral acid is 48 percent hydrobromic acid. Time and temperature are not critical factors for the conduct of this reaction, typical temperatures varying from 100°C. to reflux, and typical times being in the range of 20 minutes to several hours. This procedure is most suitable for the preparation of those compounds wherein Alk separates the nitrogen atoms attached thereto by 3 or more carbon atoms.

The cis-2,3,4,4a,9,9a-hexahydro-9-cis-phenyl compounds are prepared by catalytic hydrogenation of the 2,3-dihydro compounds of the formula

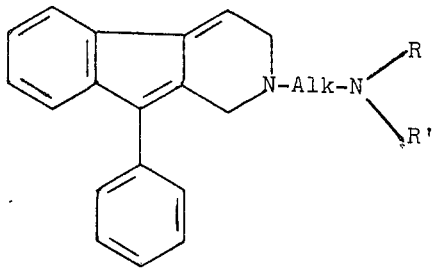

(III)

wherein Alk and NRR' are defined as hereinabove. Suitable catalysts include platinum oxide and palladium, a particularly preferred catalyst being palladium. The hydrogenation is conveniently conducted in a solvent, the choice of solvent depending on the particular starting material employed. Suitable solvents include, but are not limited to, alkanols such as methanol and ethanol, ethers such as tetrahydrofuran, and aqueous acetic acid. The reaction is generally conducted at a temperature ranging from room temperature to 100°C., with a temperature range of 50°-60°C. being typical.

The cis and trans configuration, as used in naming the compounds of this application, refer to the configuration of attachment of the pyridine and/or phenyl ring relative to the indeno ring system. Thus, in the compound, cis-2,3,4,4a,9,9a-hexahydro-9-cis-phenyl-1H-indeno[2,1-c]pyridine, the indene and pyridine rings are fused in a cis manner, and the hydrogens at the 4a, 9 and 9a positions are all on the same side of the ring system. Accordingly, in the compound, cis-2,3,4,4a,9,9a-hexahydro-9-trans-phenyl-1H-indeno[2,1-c]pyridine, the 9 phenyl substituent and the 4a and 9a hydrogens are on the same side of the ring system.

The isomeric cis-2,3,4,4a,9,9a-hexahydro-9-trans-phenyl compounds are prepared by refluxing the corresponding compound of the formula

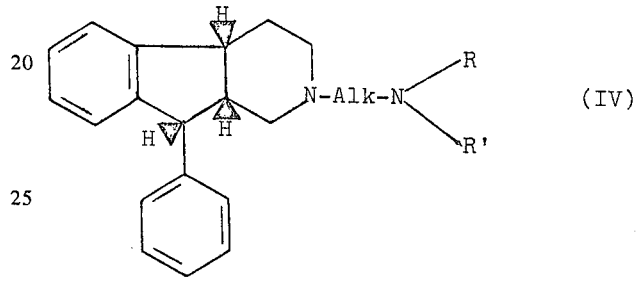

(IV)

wherein Alk and NRR' are defined as hereinabove with a solution of potassium hydroxide in n-butanol.

The present hexahydro compounds can also be prepared by contacting a compound of the formula

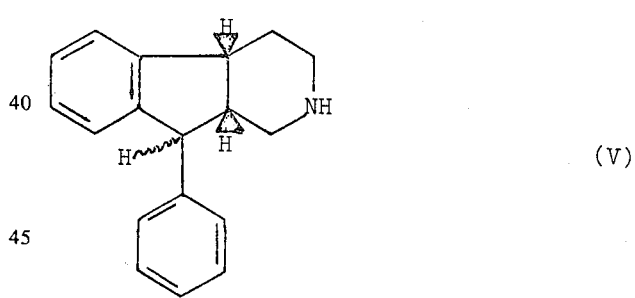

(V)

wherein the wavy line indicates the alternative cis or trans configurations, with the appropriate dialkylaminoalkyl chloride of the formula

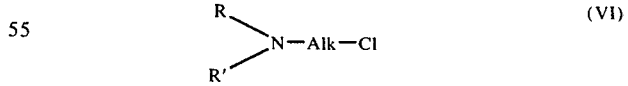

(VI)

wherein Alk and NRR' are defined as hereinabove, This reaction is conducted in a suitable solvent, preferably chloroform. Other possible solvents include aromatic hydrocarbons such as benzene and toluene, lower alkanols such as methanol and ethanol, dimethylformamide and dimethylsulfoxide. Reaction temperature can vary from room temperature to reflux, with a temperature range of 60°-70°C. being typical. Time varies from a few hours to several days. This is the preferred procedure for the preparation of those compounds wherein Alk separates the nitrogen atoms attached thereto by 2 carbon atoms.

While many of the compounds illustrated in the Examples of this invention are conveniently isolated as their salts, it is to be understood that they are usually obtained from the corresponding free base by standard chemical procedures.

The starting materials of formula (II) above can be readily prepared by condensing the appropriate diamine of the formula

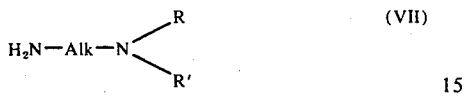

wherein Alk and NRR' are defined as hereinabove with acetophenone and formaldehyde. This reaction is conveniently conducted in a solvent. Suitable solvents include aromatic hydrocarbons such as benzene and toluene, high boiling ethers such as dioxane, lower alkanols such as methanol and ethanol, dimethylformamide, and dimethylsulfoxide. Time and temperature are not critical factors for the conduct of the reaction, typical times varying from a few hours to several days and typical temperatures being in the range of room temperature to reflux.

The starting material of formula (V) wherein the phenyl radical is in the cis configuration is conveniently prepared by debenzylation of 2,3-dihydro-2-benzyl-9-phenyl-1H-indeno[2,1-c]pyridine as described in J.C.S. Perkin I, 1, (4) 554–555(1972). The 9-trans phenyl compound may then be prepared by refluxing the 9-cis-phenyl compound in a solution of potassium hydroxide in n-butanol.

The following examples describe in detail compounds illustrative of the present invention and methods which have been devised for their preparation. It will be apparent to those skilled in the art that many modifications, both of materials and methods, may be practiced without departing from the purpose and intent of this disclosure. Throughout the examples hereinafter set forth, temperatures are given in (°C.) and relative amounts in parts by weight, except as otherwise noted.

EXAMPLE 1

To a solution of 10.2 parts of 3-dimethylaminopropylamine in 20 parts of absolute ethanol is added 17 parts by volume of concentrated hydrochloric acid. Then, 24.0 parts of acetophenone and 12.0 parts of paraformaldehyde are added, and the resulting mixture is heated to reflux. The mixture is stirred and refluxed for seven hours, and then left to stand at room temperature for about 18 hours. The solvents are then removed at 50°C. under reduced pressure to leave a semisolid that is partitioned between water and ethyl acetate. The water portion is washed once with ethyl acetate and then made alkaline by the addition of 25 parts by volume of a 25 percent by weight solution of aqueous sodium hydroxide. This mixture is stirred under a nitrogen stream to remove trace ethyl acetate. During stirring, an oil separates. After stirring for two hours, the mixture is left standing for about 18 hours. The mixture is then cooled in an ice bath and the aqueous portion removed by decantation. The residual oil is dissolved in ethyl ether, washed several times with water, and dried over anhydrous magnesium sulfate. Removal of the solvent under reduced pressure affords a tan solid. This solid is recrystallized from ethyl acetate-hexane to afford 1-(3-dimethylaminopropyl)-3-benzoyl-4-hydroxy-4-phenylpiperidine, melting at about 113.5°–115.5°C. and represented by the following structural formula.

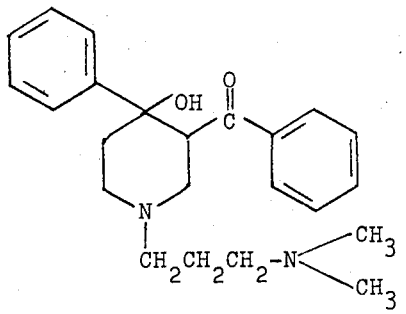

EXAMPLE 2

To 250 parts by volume of 4 M solution of hydrogen chloride in absolute ethanol is added 65.1 parts of 3-diethylaminopropylamine. Then, 120.0 parts of acetophenone and 60.0 parts of paraformaldehyde is added and the mixture heated to reflux. After stirring and refluxing for 24 hours, the solvent is removed under reduced pressure. The resulting oil is dissolved in water and washed with portions of ethyl ether. The solution is made alkaline (~pH 12) with 50 percent by weight aqueous sodium hydroxide and stirred at room temperature for 2.5 hours. During stirring, an oil separates out. This oil is purified by dissolving in isopropanol and adding to the solution a solution of hydrogen chloride in isopropanol. The resulting salt is separated by filtration, and dissolved in water. The aqueous solution of the salt is extracted several times with ethyl ether, made alkaline with 50 percent by weight aqueous sodium hydroxide solution and then extracted with ethyl acetate. The ethyl acetate fractions are combined, dried over anhydrous sodium sulfate and the solvent removed under reduced pressure. Ethyl ether is added to the residual oil and, upon cooling, crystals of 1-(3-diethylaminopropyl)-3-benzoyl-4-hydroxy-4-phenylpiperidine precipitate. This compound, after filtration and drying, melts at 76°–78°C.

EXAMPLE 3

Substitution of an equivalent amount of 3-piperidinopropylamine for the 3-dimethylaminopropylamine used in Example 1 and substantial repetition of the procedure detailed therein affords 1-(3-piperidinopropyl)-3-benzoyl-4-hydroxy-4-phenylpiperidine. After recrystallization from chloroform and ethyl ether this compound melts at 122°–123°C. and is represented by the following structural formula

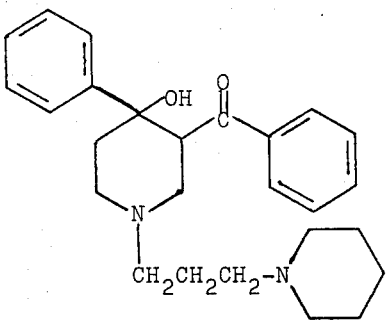

EXAMPLE 4

When an equivalent amount of 2-dimethylaminoethylamine is substituted for the 3-dimethylaminopropylamine used in Example 1 and the procedure detailed therein substantially repeated, there is obtained 1-(2-dimethylaminoethyl)-3-benzoyl-4-hydroxy-4-phenylpiperidine. This product melts at 101°–102°C.

EXAMPLE 5

Substitution of an equivalent quantity of benzylamine for the 3-dimethylaminopropylamine used in Example 1 and repetition of the procedure detailed therein affords 1-benzyl-3-benzoyl-4-hydroxy-4-phenylpiperidine, melting at about 116°–118°C.

EXAMPLE 6

A mixture of 15.1 parts of 1-(3-dimethylaminopropyl)-3-benzoyl-4-hydroxy-4-phenylpiperidine and 75 parts by volume of 48 percent hydrobromic acid is stirred and gradually warmed to 120°C. over a period of 3.5 hours. Water is then added and the solvent removed under reduced pressure. Acetone is added and removed under reduced pressure until a filterable solid is obtained. The solid is filtered, washed with portions of ethyl ether, and air-dried to give a yellow powder. Recrystallization from acetic acid affords, as yellow crystals, 2,3-dihydro-2-(3-dimethylaminopropyl-9-phenyl-1H-indeno[2,1-c]pyridine dihydrobromide hemihydrate, which becomes a glass at 65°–70°C. and darkens at a temperature >120°C. The free base of this compound is represented by the following structural formula.

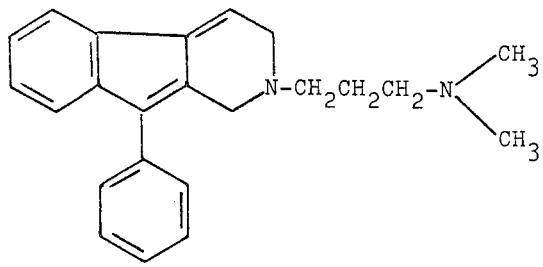

EXAMPLE 7

A mixture of 20.0 parts of 1-(3-diethylaminopropyl)-3-benzoyl-4-hydroxy-4-phenylpiperidine and 100 parts by volume of 48 percent hydrobromic acid is refluxed for 2.5 hours. After cooling to room temperature, the solvent is removed under reduced pressure and acetone repeatedly added and removed under reduced pressure. The resulting yellow solid is recrystallized from 50:50 methanol-ether and dried at 90°C. for 5 hours to afford 2,3-dihydro-2-(3-diethylaminopropyl)-9-phenyl-1H-indeno[2,1-c]pyridine dihydrobromide containing 1½ moles of water of hydration per mole. This compound melts at 136°–138°C.

EXAMPLE 8

Substitution of an equivalent quantity of 1-(3-piperidinopropyl)-3-benzoyl-4-hydroxy-4-phenyl-piperidine for the 1-(3-dimethylaminopropyl)-3-benzoyl-4hydroxy-4-phenylpiperidine used in Example 7, and repetition of the procedure detailed therein, affords 2,3-dihydro-2-(3-piperidinopropyl)-9-phenyl-1H-indeno[2,1-c]pyridine dihydrobromide hydrate. This compound melts at 178°–180°C. and is represented by the following structural formula.

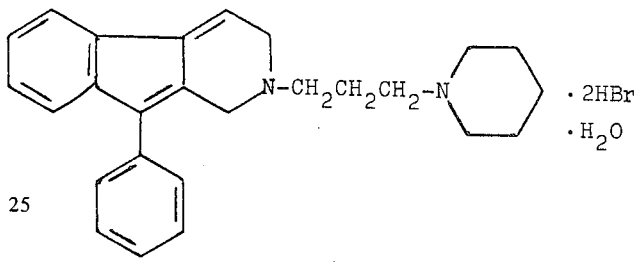

EXAMPLE 9

When an equivalent amount of 1-benzyl-3-benzoyl-4-hydroxy-4-phenylpiperidine is substituted for the 1-(3-dimethylaminopropyl)-3-benzoyl-4-hydroxy-4-phenylpiperidine used in Example 2 and the procedure detailed therein repeated, there is obtained 2,3-dihydro-2-benzyl-9-phenyl-1H-indeno[2,1-c]pyridine hydrobromide, melting at 189°–192°C.

EXAMPLE 10

9.0 Parts of 2,3-dihydro-2-(3-dimethylaminopropyl)-9-phenyl-1H-indeno[2,1-c]pyridine dihydrobromide hemihydrate is dissolved in approximately 74 parts by volume of a 50 percent ethanol solution in a Parr Shaker. A mixture of 0.33 part palladium chloride and 0.24 part of sodium chloride in 3.7 parts water is added dropwise. Then 0.56 part sodium borohydride in 5.5 parts water is added and the mixture is shaken at 60°C. and a pressure of 60 psi for approximately 8 hours. The catalyst is removed by filtration and the yellow filtrate is concentrated under reduced pressure to give a thick oil. The oil is dissolved in water and the solution made alkaline with potassium carbonate. The oil that separates is extracted with portions of ethyl ether and the extracts combined and dried over anhydrous magnesium sulfate. The ethyl ether is removed under reduced pressure to give a clear oil. This oil is dissolved in isopropanol and treated with a solution of hydrogen chloride in isopropanol. Ethyl ether is then added and the resulting precipitate filtered. The off-white solid is recrystallized from absolute ethanol. Further recrystallizations from a mixture of glacial acetic acid and ethyl ether, and water, followed by drying in vacuo over refluxing benzene affords cis-2,3,4,4a,9,9a-hexahydro-2-(3-dimethylaminopropyl)-9-cis-phenyl-1H-indeno[2,1-c]pyridine dihydrochloride hydrate, melting at 254.5°–258°C. and represented by the following structural formula.

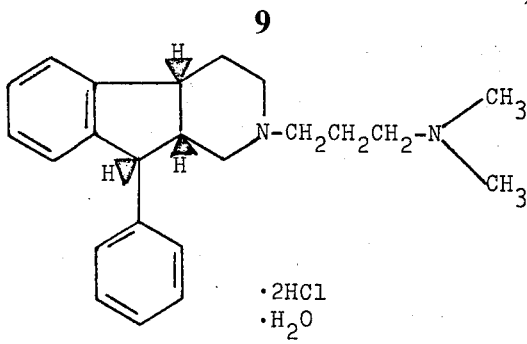

·2HCl
·H₂O

EXAMPLE 11

8.32 Parts of 2,3-dihydro-2-(3-diethylaminopropyl)-9-phenyl-1H-indeno[2,1-c]pyridine dihydrobromide is dissolved in approximately 74 parts by volume of a 50 percent ethanol solution in a Parr Shaker. Then, 0.8 part of palladium catalyst is added and the mixture shaken at 60 psi for approximately 2 hours. The catalyst is removed by filtration and the filtrate concentrated under reduced pressure. Water is added to the residue, the solution is basified with potassium carbonate, and then is extracted with ethyl ether. The ether extracts are combined and dried over anhydrous magnesium sulfate. Treatment with a solution of hydrogen chloride in isopropanol results in an oil. The solvents are removed by decantation and ethyl ether added. Ethanol is added until the solution clears and ethyl ether is again added until the solution begins to cloud. The resulting crystals, cis-2,3,4,4a,9,9a-hexahydro-2-(3-diethylaminopropyl)-9-cis-phenyl-1H-indeno[2,1-c]pyridine dihydrochloride hemihydrate, melt at 220°-230°C.

EXAMPLE 12

When an equivalent quantity of 2,3-dihydro-2-(3-piperidinopropyl)-9-phenyl-1H-indeno[2,1-c]pyridine dihydrobromide hydrate is substituted for the 2,3-dihydro-2-(3-diethylaminopropyl)-9-phenyl-1H-indeno[2,1-c]pyridine dihydrobromide hemihydrate of Example 11, and the procedure detailed therein substantially repeated, there is obtained cis-2,3,4,4a9,9a-hexahydro-2-(3-piperidinopropyl)-9-cis-phenyl-1H-indeno[2,1-c]pyridine dihydrochloride hemihydrate, decomposing at 275°C. The free base of this compound is represented by the following structural formula.

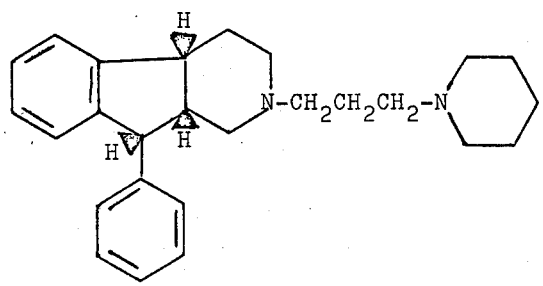

EXAMPLE 13

15.44 Parts of 2,3-dihydro-2-benzyl-9-phenyl-1H-indeno[2,1-c]pyridine hydrobromide is dissolved in 750 parts by volume of a 50 percent ethanol solution in a Parr Shaker. Then, 1.5 parts of palladium catalyst is added and the mixture is shaken at 60°C. and a pressure of 51 psi for approximately 11 hours. The catalyst is removed by filtration and the filtrate is concentrated under reduced pressure to give an oil. This oil is dissolved in chloroform. The volume of the solution is then reduced to a minimum by distilling off the chloroform, and ethyl ether added until the solution becomes turbid. The resulting solid is then filtered and recrystallized from chloroform and ethyl ether to afford cis-2,3,4,4a,9,9a-hexahydro-9-cis-phenyl-1H-indeno[2,1-c]pyridine hydrobromide hemihydrate. This compound softens at 145°C., melts at 192°-195°C., and is represented by the structural formula given below.

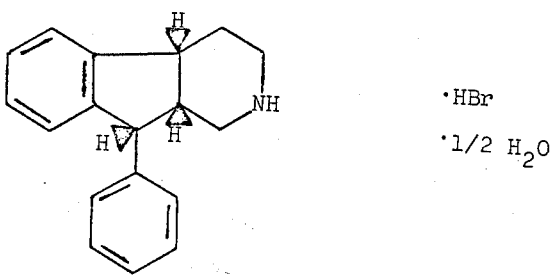

·HBr
·1/2 H₂O

EXAMPLE 14

To a solution of 2.0 parts of cis-2,3,4,4a,9,9a-hexahydro-9-cis-phenyl-1H-indeno[2,1-c]pyridine and 5.0 parts of triethylamine in 75 parts of chloroform is slowly added 5.43 parts of 2-diethylaminoethyl chloride. The reaction mixture is refluxed for 6 hours and left to stand for 18 hours at room temperature. The mixture is then washed twice with water and the organic layer separated. The organic layer is dried over anhydrous magnesium sulfate and stripped of solvent under reduced pressure to leave as an oil, cis-2,3,4,4a,9,9a-hexahydro-2-(2-diethylaminoethyl)-9-cis-phenyl-1H-indeno[2,1-c]pyridine. After dissolving this oil in ethyl ether a solution of hydrogen bromide in acetic acid is then added dropwise. The resulting precipitate is filtered and recrystallized from chloroform and ethyl ether to give cis-2,3,4,4a,9,9a-hexahydro-2-(2-diethylaminoethyl)-9-cis-phenyl-1H-indeno[2,1-c]pyridine dihydrobromide containing 1½ moles of water of hydration per mole. This compound melts at 132°-135°C.

EXAMPLE 15

When an equivalent amount of 2-dimethylaminoethyl chloride is substituted for the 2-diethylaminoethyl chloride of Example 14, and the procedure detailed therein substantially repeated, there is obtained cis-2,3,4,4a,9,9a-hexahydro-2-(2-dimethylaminoethyl)-9-cis-phenyl-1H-indeno[2,1-c]pyridine dihydrobromide.

EXAMPLE 16

Substitution of an equivalent quantity of 3-hexamethyleneiminopropyl chloride or 3-diisopropylaminopropyl chloride for the 2-diethylaminoethyl chloride of Example 14 and substantial repetition of the procedure detailed therein affords cis-2,3,4,4a,9,9a-hexahydro-2-(3-hexamethyleneiminopropyl)-9-cis-phenyl-1H-indeno[2,1-c]pyridine dihydrobromide and cis-2,3,4,4a,9,9a-hexahydro-2-(3-diisopropylaminopropyl)-9-cis-phenyl-1H-indeno[2,1-c]pyridine dihydrobromide, respectively.

EXAMPLE 17

A solution of 3.28 parts of cis-2,3,4,4a,9,9a-hexahydro-2-(3-dimethylaminopropyl)-9-cis-phenyl-1H-indeno[2,1-c]pyridine dihydrochloride hydrate in 65 parts by volume of a 25 percent w/v solution of potassium hydroxide in n-butanol is stirred at reflux for approximately 18 hours. Part of the solvent is then removed under reduced pressure and the resulting mixture poured into ice water. The oil which separates is extracted with ethyl ether. The extracts are combined, washed with several portions of water, and dried over anhydrous magnesium sulfate. Removal of the solvent under reduced pressure affords as a greenish oil, cis-2,3,4,4a,9,9a-hexahydro-2-(3-dimethylaminopropyl)-9-trans-phenyl-1H-indeno[2,1-c]pyridine, which is dissolved in isopropanol and treated with a solution of hydrogen chloride in isopropanol. The resulting solid is collected by filtration, washed with several portions of ethyl ether, and air-dried. The white crystals are recrystallized from absolute ethanol and ethyl acetate to give cis-2,3,4,4a,9,9a-hexahydro-2-(3-dimethylaminopropyl)-9-trans-phenyl-1H-indeno[2,1-c]pyridine dihydrochloride hemihydrate melting at about 268.5°–270°C., and represented by the following structural formula.

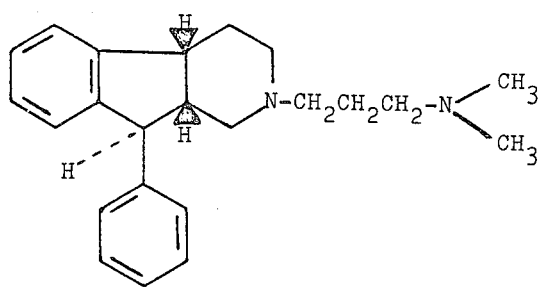

EXAMPLE 18

3.2 Parts of cis-2,3,4,4a,9,9a-hexahydro-2-(3-diethylaminopropyl)-9-cis-phenyl-1H-indeno[2,1-c]pyridine dihydrochloride hemihydrate is dissolved in 75 parts by volume of a 25 percent w/v solution of potassium hydroxide in n-butanol and stirred at reflux for about 18 hours. Part of the solvent is removed under reduced pressure and the resulting mixture poured into ice water. The oil which separates is extracted three times with portions of ethyl ether. The extracts are combined, washed with water, and dried over anhydrous magnesium sulfate. A solution of hydrogen chloride in isopropanol is added, causing the formation of an oil. The solvent is decanted off and fresh ethyl ether added. Scratching of the solution results in a hydroscopic solid product. This product is neutralized with sodium hydroxide solution dissolved in ethyl ether, and a mixture of hydrogen bromide and acetic acid is added. The resulting solid is separated and recrystallized from methanol and ethyl ether to give cis-2,3,4,4a,9,9a-hexahydro-2-(3-diethylaminopropyl-9-trans-phenyl-1H-indeno[2,1-c]pyridine dihydrobromide hydrate melting at 117°–119°C.

EXAMPLE 19

Substitution of an equivalent amount of cis-2,3,4,4a,9,9a-hexahydro-2-(3-piperidinopropyl)-9-cis-phenyl-1H-indeno[2,1-c]pyridine dihydrochloride hemihydrate for the cis-2,3,4,4a,9,9a-hexahydro-2-(3-dimethylaminopropyl)-9-cis-phenyl-1H-indeno[2,1-c]pyridine dihydrochloride hydrate used in Example 17 and substantial repetition of the procedure detailed therein, affords cis-2,3,4,4a,9,9a-hexahydro-2-(3-piperidinopropyl)-9-transphenyl-1H-indeno[2,1-c]pyridine dihydrochloride hemihydrate, melting at about 190°–192°C. The free base of this compound is represented by the following structural formula.

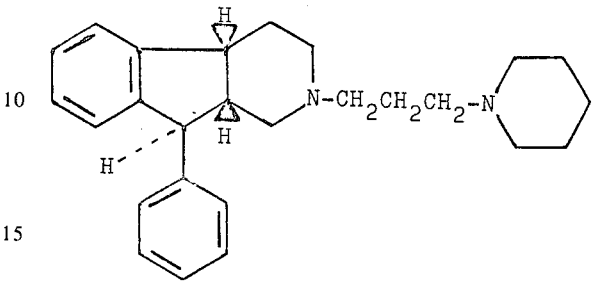

EXAMPLE 20

When an equivalent quantity of cis-2,3,4,4a,9,9a-hexahydro-9-cis-phenyl-1H-indeno[2,1-c]pyridine hydrobromide hemihydrate is substituted for the cis-2,3,4,4a,9,9a-hexahydro-2-(3-dimethylaminopropyl)-9-cis-phenyl-1H-indeno[2,1-c]-pyridine dihydrochloride hydrate of Example 17, and the procedure detailed therein substantially repeated, there is obtained cis-2,3,4,4a,9,9a-hexahydro-9-trans-phenyl-1H-indeno[2,1-c]pyridine hydrochloride, melting at 258°–260°C.

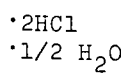

EXAMPLE 21

When an equivalent amount of cis-2,3,4,4a,9,9a-hexahydro-9-trans-phenyl-1H-indeno[2,1-c]pyridine is substituted for the cis-2,3,4,4a,9,9a-hexahydro-9-cis-phenyl-1H-indeno[2,1-c]pyridine of Example 14 and the procedure detailed therein substantially repeated, there is obtained cis-2,3,4,4a,9,9a-hexahydro-2-(2-diethylaminoethyl)-9-trans-phenyl-1H-indeno[2,1-c]pyridine dihydrobromide hydrate. This compound melts at 135°–138°C. after recrystallization from chloroform and ethyl ether.

EXAMPLE 22

Substitution of equivalent quantities of cis-2,3,4,4a,9,9a-hexahydro-9-trans-phenyl-1H-indeno[2,1-c]pyridine and 2-dimethylaminoethyl chloride for the cis-2,3,4,4a,9,9a-hexahydro-9-cis-phenyl-1H-indeno[2,1-c]pyridine and 2-diethylaminoethyl chloride of Example 14 and substantial repetition of the procedure detailed therein affords cis-2,3,4,4a,9,9a-hexahydro-2-(2-dimethylaminoethyl)-9-trans-phenyl-1H-indeno[2,1-c]pyridine dihydrobromide, melting at 238°–240°C. after recrystallization from chloroform and ethyl ether.

EXAMPLE 23

When equivalent amounts of cis-2,3,4,4a,9,9a-hexahydro-9-trans-phenyl-1H-indeno[2,1-c]pyridine and 2-pyrrolidinoethyl chloride are substituted for the cis- 2,3,4,4a,9,9a-hexahydro-9-cis-phenyl-1H-indeno[2,1-c]pyridine and 2-diethylaminoethyl chloride of Example 14 and the procedure detailed therein substantially repeated, there is obtained cis-2,3,4,4a,9,9a-hexahydro-2-(2-pyrrolidinoethyl)-9-trans-phenyl-1H-indeno[2,1-c]pyridine dihydrobromide.

What is claimed is:
1. A compound of the formula

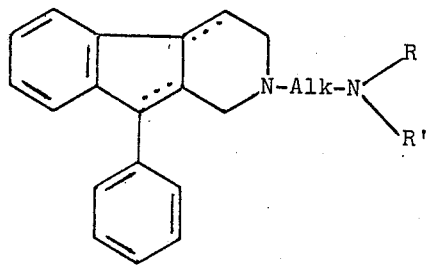

(I)

wherein Alk is alkylene of 2 to 6 carbon atoms separating the nitrogen atoms attached thereto by at least 2 carbon atoms; NRR' is selected from the group consisting of di(lower alkyl)amino, pyrrolidino, piperidino, and hexamethyleneimino; and the dotted lines indicate the optional presence of a set of double bonds.

2. A compound according to claim 1 which is 2,3-dihydro-2-(3-dimethylaminopropyl)-9-phenyl-1H-indeno[2,1-c]pyridine.

3. A compound according to claim 1 which is 2-(3-diethylaminopropyl)-2,3-dihydro-9-phenyl-1H-indeno[2,1-c]pyridine.

4. A compound according to claim 1 which is 2,3-dihydro-2-(3-piperidinopropyl)-9-phenyl-1H-indeno[2,1-c]pyridine.

5. A compound according to claim 1 of the formula

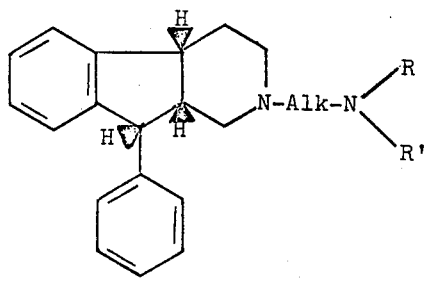

wherein Alk is alkylene of 2–6 carbon atoms and NRR' is selected from the group consisting of di(lower alkyl)amino, pyrrolidino, piperidino and hexamethyleneimino.

6. A compound according to claim 1 which is cis-2,3,4,4a,9,9a-hexahydro-2-(2-dimethylaminoethyl)-9-cis-phenyl-1H-indeno[2,1-c]pyridine.

7. A compound according to claim 1 which is cis-2,3,4,4a,9,9a-hexahydro-2-(2-diethylaminoethyl)-9-cis-phenyl-1H-indeno[2,1-c]pyridine.

8. A compound according to claim 1 which is cis-2,3,4,4a,9,9a-hexahydro-2-(3-dimethylaminopropyl)-9-cis-phenyl-1H-indeno[2,1-c]pyridine.

9. A compound according to claim 1 which is cis-2,3,4,4a,9,9a-hexahydro-2-(3-diethylaminopropyl)-9-cis-phenyl-1H-indeno[2,1-c]pyridine.

10. A compound according to claim 1 which is cis-2,3,4,4a,9,9a-hexahydro-2-(3-piperidinopropyl)-9-cis-phenyl-1H-indeno[2,1-c]pyridine.

11. A compound according to claim 1 of the formula

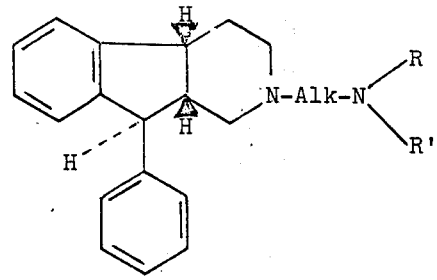

wherein Alk is alkylene of 2–6 carbon atoms and NRR' is selected from the group consisting of di(lower alkyl)amino, pyrrolidino, piperidino, and hexamethyleneimino.

12. A compound according to claim 1 which is cis-2,3,4,4a,9,9a-hexahydro-2-(2-dimethylaminoethyl)-9-trans-phenyl-1H-indeno[2,1-c]pyridine.

13. A compound according to claim 1 which is cis-2,3,4,4a,9,9a-hexahydro-2-(2-diethylaminoethyl)-9-trans-phenyl-1H-indeno[2,1-c]pyridine.

14. A compound according to claim 1 which is cis-2,3,4,4a,9,9a-hexahydro-2-(3-diethylaminopropyl)-9-trans-phenyl-1H-indeno[2,1-c]pyridine.

15. A compound according to claim 1 which is cis-2,3,4,4a,9,9a-hexahydro-2-(3-piperidinopropyl)-9-trans-phenyl-1H-indeno[2,1-c]pyridine.

* * * * *